US00PP29198P2

(12) United States Plant Patent
Smit

(10) Patent No.: US PP29,198 P2
(45) Date of Patent: Apr. 3, 2018

(54) ***ECHEVERIA* PLANT NAMED 'EC-ECH-02'**

(50) Latin Name: ***Echeveria gigantea*×*E. pulidonis***
Varietal Denomination: EC-ECH-02

(71) Applicant: Obed Jacob Smit, Sappemeer (NL)

(72) Inventor: Obed Jacob Smit, Sappemeer (NL)

(73) Assignee: Eden Collection B.V., Sappemeer (NL)

( * ) Notice: Subject to any disclaimer, the term of this patent is extended or adjusted under 35 U.S.C. 154(b) by 59 days.

(21) Appl. No.: 15/330,377

(22) Filed: Sep. 12, 2016

(51) Int. Cl.
*A01H 5/02* (2018.01)
*A01H 5/12* (2018.01)

(52) U.S. Cl.
USPC ..... Plt./373
CPC ..... *A01H 5/12* (2013.01)

(58) Field of Classification Search
USPC ..... Plt./373
See application file for complete search history.

*Primary Examiner* — Keith O Robinson

(57) ABSTRACT

A new cultivar of *Echeveria* plant named 'EC-ECH-02' that is characterized by blue-green leaves with red margins and a rosette plant form.

1 Drawing Sheet

Botanical classification: *Echeveria gigantea*×*E. pulidonis*.

Variety denomination: 'EC-ECH-02'.

BACKGROUND OF THE INVENTION

The present invention relates to a new and distinct cultivar of *Echeveria* plant botanically known as *Echeveria gigantea*×*E. pulidonis* and hereinafter referred to by the cultivar name 'EC-ECH-02'.

'EC-ECH-02' originated from the crossing of the female or seed parent, an unnamed *Echeveria gigantea* cultivar and the male or pollen parent, an unnamed *Echeveria pulidonis* cultivar. The crossing was conducted in 2013 in Sappemeer, Netherlands. The resulting seeds were subsequently planted and grown. The cultivar 'EC-ECH-02' was selected by the inventor in 2014 in a controlled environment as a single plant within the progeny of the stated cross in a cultivated area of Sappemeer, Netherlands.

Asexual reproduction of the new cultivar 'EC-ECH-02' first occurred by leaf cuttings in 2014 in Sappemeer, Netherlands. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Echeveria* cultivar 'EC-ECH-02'. These traits in combination distinguish 'EC-ECH-02' as a new and distinct cultivar apart from other existing varieties of *Echeveria* known by the inventor.

1. *Echeveria* 'EC-ECH-02' exhibits blue-green leaves with red margins.
2. *Echeveria* 'EC-ECH-02' exhibits a rosette plant form.

The closest comparison cultivars are *Echeveria* 'Miranda' (not patented) and *Echeveria* 'Hercules' (U.S. Plant Pat. No. 26,230) 'EC-ECH-02' is distinguishable from 'Miranda' by the following characteristics:

1. *Echeveria* 'EC-ECH-02' exhibits blue-green leaves. In comparison, the leaves of 'Miranda' are green.

2. *Echeveria* 'EC-ECH-02' exhibits leaves with red margins. In comparison, the margins of 'Miranda' are the same color as the leaves.
3. *Echeveria* 'EC-ECH-02' exhibits a rounded leaf shape. In comparison, 'Miranda' has leaves with a pointed leaf shape.

'EC-ECH-02' is distinguishable from 'Hercules' by the following characteristics:

1. *Echeveria* 'EC-ECH-02' exhibits larger leaves than the leaves of 'Hercules'.
2. *Echeveria* 'EC-ECH-02' exhibits a less number of leaves than the number of leaves of 'Hercules'.

'EC-ECH-02' is distinguishable from the female parent plant, an unnamed *Echeveria gigantea* cultivar, by the following characteristics:

1. 'EC-ECH-02' has a larger number of leaves than the female parent plant.

'EC-ECH-02' is distinguishable from the male parent plant, an unnamed *Echeveria pulidonis* cultivar by the following characteristics:

1. The leaves of 'EC-ECH-02' exhibit a more elongated leaf shape than the leaves of the male parent plant.
2. The leaves of 'EC-ECH-02' have red margins. In comparison, the leaf margins of the male parent plant are darker red in color.

BRIEF DESCRIPTION OF THE DRAWING

The accompanying photographs illustrate the distinguishing traits of *Echeveria* 'EC-ECH-02'.

FIG. 1 shows an overall view of a 25 week old plant.

The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Echeveria* cultivar named 'EC-ECH-02'. Data was collected in Sappemeer, Netherlands from 25 week old plants grown in a glass greenhouse in 12 cm. diameter containers. The time of year was Winter and the temperature range was 18-25 degrees Centigrade during the day and 12-18 degrees Centigrade at night. The light level was natural light level. No photoperiodic treatments or growth retardants were used. Color determinations are in accordance with The Royal Horticultural Society Colour Chart 2015 edition, except where general color terms of ordinary dictionary significance are used. The growing requirements are similar to the species. 'EC-ECH-02' has not been tested under all possible conditions and phenotypic differences may be observed with variations in environmental, climatic, and cultural conditions, however, without any variance in genotype.

Botanical classification: *Echeveria gigantea*×*E. pulidonis* 'EC-ECH-02'.

Annual or perennial: Perennial.

Parentage: 'EC-ECH-02' is a hybrid of the female parent, an unnamed *Echeveria gigantea* cultivar and the male or pollen parent, an unnamed *Echeveria pulidonis* cultivar.

Plant type: Pot plant.

Plant shape: Basal rosette, no branching.

Suitable container size: 7 cm. pots or larger.

Plant height: 6.6 cm.

Plant width: 16.9 cm.

Vigor: Moderate.

Low temperature tolerance: 5° Centigrade.

High temperature tolerance: 40° Centigrade.

Propagation: Leaf cuttings.

Time to initiate roots (summer): 7 days at 25° C.

Time to initiate roots (winter): 14 days at 18° C.

Time to produce a rooted cutting: Leaf cuttings are placed directly into growing container.

Growth rate: Moderate.

Crop time: Approximately 20 to 25 weeks from June to November in Sappemeer, Netherlands.

Root system: Fibrous.

Root color: N155.

Plant fragrance: None.

Foliage:

*Leaf arrangement*.—Basal rosette.

*Compound or single*.—Single.

*Quantity of leaves per plant*.—Average 23.

*Leaf shape*.—Spathulate.

*Leaf aspect*.—Flat to slightly concave.

*Leaf apex*.—Rounded with a small acute outer tip.

*Leaf base*.—Attenuate.

*Leaf dimensions*.—8.4 cm. in length and 5.2 cm. in width.

*Leaf thickness*.—0.5 cm.

*Texture*.—Glabrous both surfaces, succulent.

*Pubescence*.—Absent.

*Leaf margin*.—Entire.

*Venation pattern*.—None visible.

*Young leaf color* (*upper surface*).—NN137B, margins 182A, covered with thin waxy layer 188A to 188B.

*Young leaf color* (*lower surface*).—NN137B, margins 182A, covered with thin waxy layer 188A to 188B.

*Mature leaf color* (*upper surface*).—NN137A, margins 183A to 183B, covered with thin waxy layer 188B.

*Mature leaf color* (*lower surface*).—NN137B, base 147D, margins 183A to 183B, covered with thin waxy layer 188B.

*Leaf attachment*.—Sessile.

Flower: 'EC-ECH-02' has not produced flowers to date.

Fruit and seed: 'EC-ECH-02' has not produced fruit or seed to date.

Disease and pest resistance: Disease and pest resistance has not been observed.

The invention claimed is:

1. A new and distinct variety of *Echeveria* plant named 'EC-ECH-02' as described and illustrated.

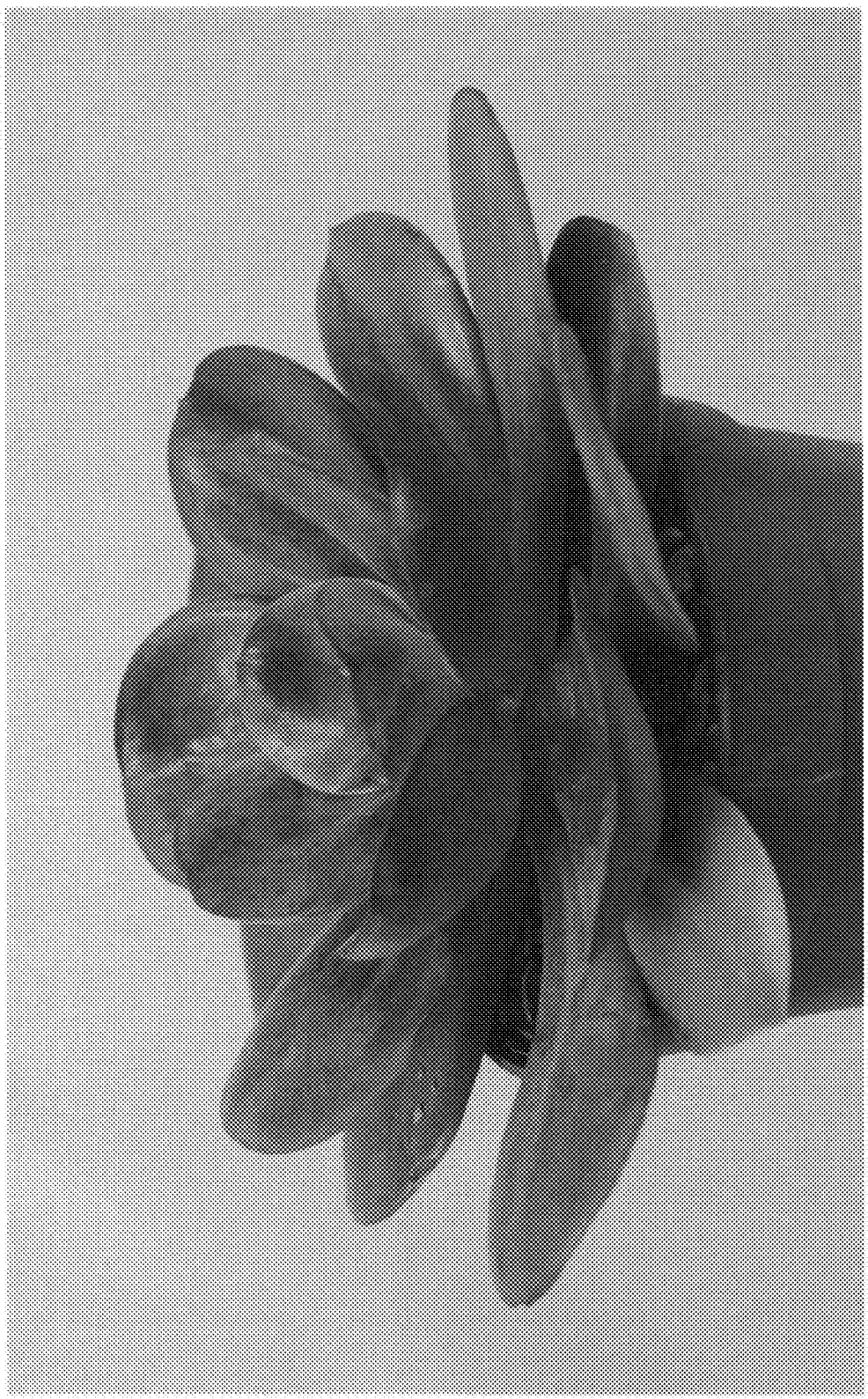

* * * * *